United States Patent [19]

Tamura

[11] 4,338,174

[45] Jul. 6, 1982

[54] ELECTROCHEMICAL SENSOR WITH TEMPERATURE COMPENSATION MEANS

[75] Inventor: Paul S. Tamura, Irvine, Calif.

[73] Assignee: McNeilab, Inc., Fort Washington, Pa.

[21] Appl. No.: 1,507

[22] Filed: Jan. 8, 1979

[51] Int. Cl.³ .............................................. G01N 27/30
[52] U.S. Cl. ................................ 204/195 P; 128/635; 338/22 R; 338/22 SD
[58] Field of Search ................ 204/195 P, 195 B, 1 P; 128/2 E, 2.1 E; 324/29; 338/22 R, 22 SD

[56] References Cited

U.S. PATENT DOCUMENTS

| | | | |
|---|---|---|---|
| 3,227,643 | 1/1966 | Okun et al. ...................... | 204/195 P |
| 3,826,730 | 7/1974 | Watanabe et al. .............. | 204/195 P |
| 4,057,478 | 11/1977 | Bruckenstein et al. ......... | 204/195 P |

FOREIGN PATENT DOCUMENTS 726863   2/1966   Canada ............................ 204/195 P

*Primary Examiner*—G. L. Kaplan
*Attorney, Agent, or Firm*—Audley A. Ciamporcero, Jr.

[57] ABSTRACT

A disposable gas sensor, such as for monitoring $pO_2$ in blood or administered gases, includes a housing, a passageway therein for blood or gas, a membrane-anode-cathode polarographic assembly, and a temperature sensing element. The temperature sensing element penetrates the housing and includes a removable thermistor, which is matable with the housing for thermal contact with a metallic element, and which in turn is in direct contact with the fluid being monitored.

5 Claims, 4 Drawing Figures

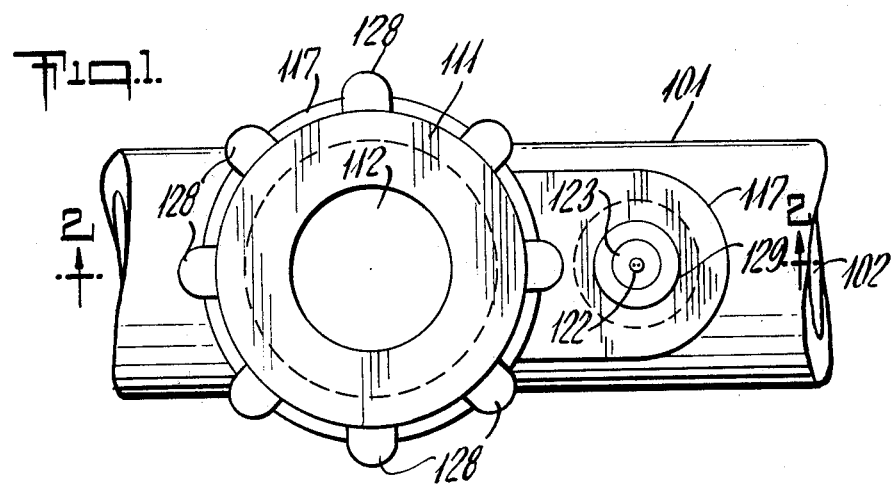
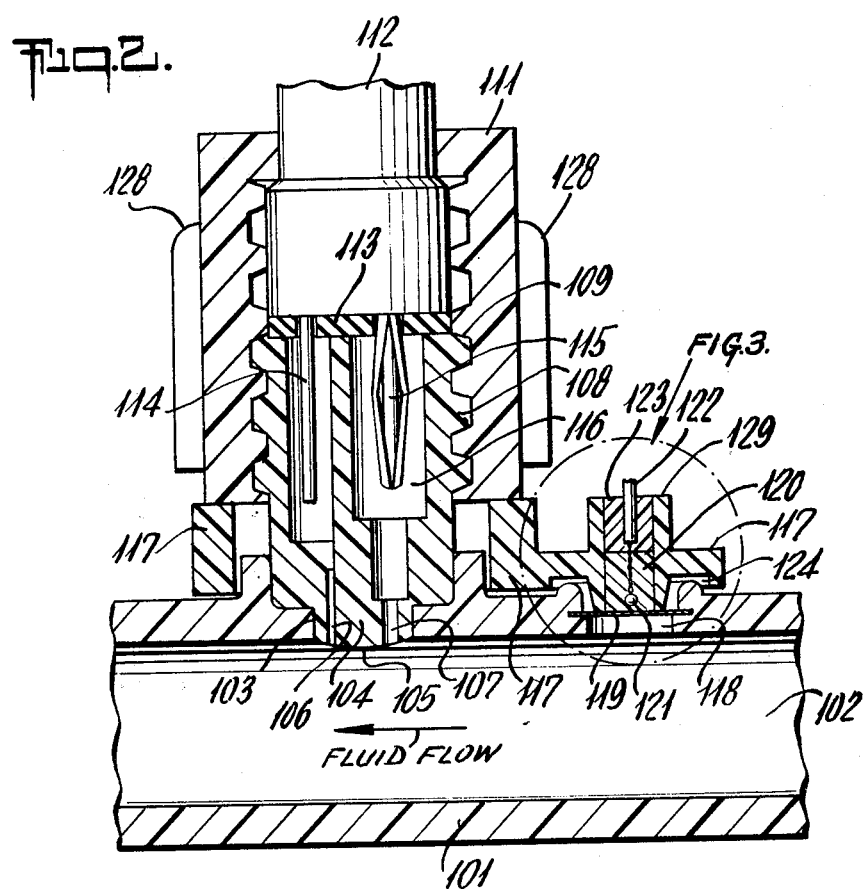

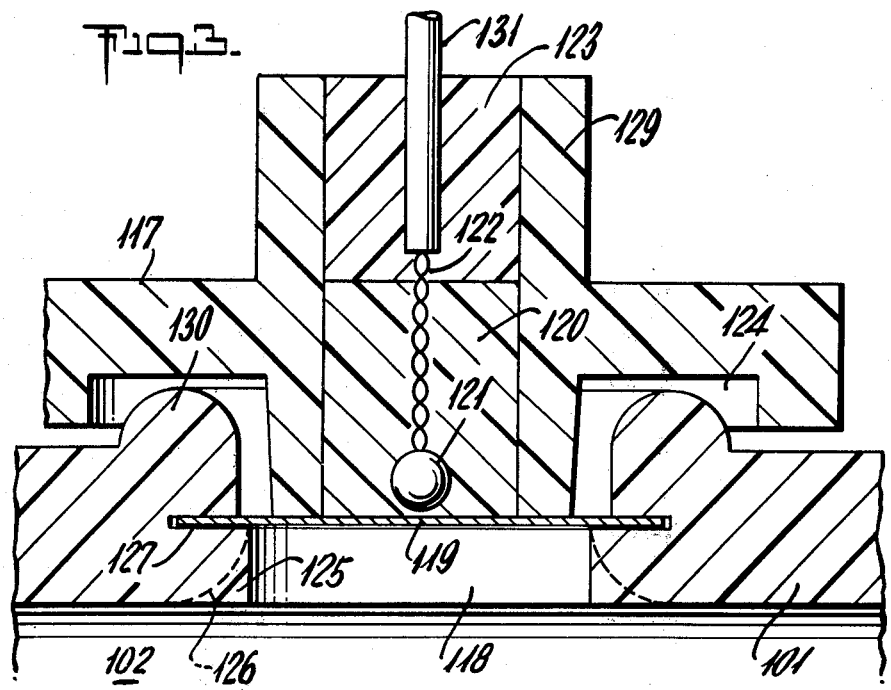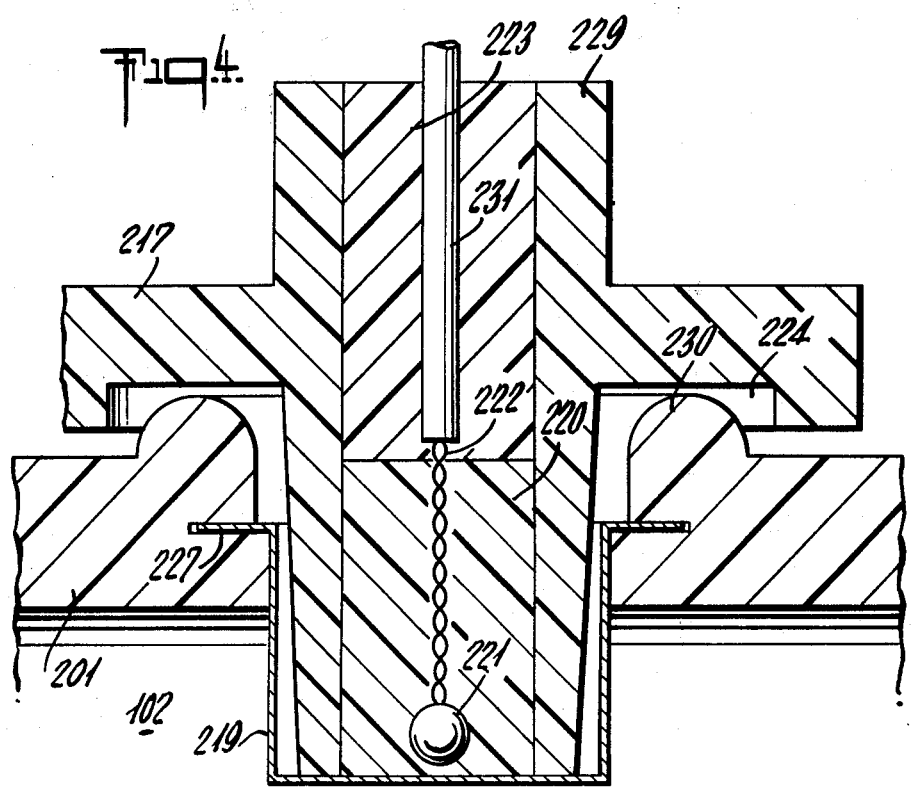

ELECTROCHEMICAL SENSOR WITH TEMPERATURE COMPENSATION MEANS

FIELD OF THE INVENTION

This invention relates to electrochemical sensors such as polarographic electrodes, and more particularly to disposable electrochemical sensors including discrete thermal sensing and compensating aspects.

PRIOR ART AND BACKGROUND

In the course of delivery of health care services, it is often important to measure accurately the amounts of particular types of gases in the fluid in question. For example, during surgery, it is important to measure partial pressures of oxygen ($pO_2$), carbon dioxide ($pCO_2$), pH, and the like blood parameters, and likewise to sense some or all of such parameters in the gas mixture administered for anesthesia. Accurate monitoring of these gases, in the blood or in the anesthesia mixture, allows for accurate control or alteration of the gases administered to the patients. Similar needs often arise in intensive care units.

Most gas monitoring equipment utilizes electrochemical techniques for monitoring of gases, for example of oxygen. Most oxygen monitoring equipment involves the polarographic principle, in which an electrochemical cell is driven by a constant polarizing voltage, and the current through the cell, under proper conditions, is proportional to the amount of oxygen available to the cell. A typical oxygen electrode is shown in U.S. Pat. No. 3,826,730 to H. Watanabe et al, entitled "Disposable Electrochemical Electrode" and assigned to the assignee hereof. That patent sets forth an electrode wherein an anode and a cathode are carried in respective electrolytes and separated from the fluid being monitored by a selective gas permeable membrane. An electrical circuit is constituted by the cathode (generally a noble metal, such as gold, platinum, or silver), the electrolyte (such as saline electrolyte or potassium chloride solution), and the anode (such as silver). To the extent that oxygen is present in the fluid being monitored, it correspondingly penetrates the oxygen permeable membrane, and promotes the chemical reaction:

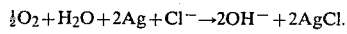

$$\tfrac{1}{2}O_2 + H_2O + 2Ag + Cl^- \rightarrow 2OH^- + 2AgCl.$$

The rate of this reaction is determined by several factors, including oxygen pressure at the cathode, cathode surface area (assuming the anode is large), membrane permeability and thickness, electrode geometry, and temperature. The factors of anode and cathode size, membrane properties, and electrode geometry are carefully controlled during the manufacturing process so that only oxygen pressure and the overall temperature affect the output of the electrode. Conventionally, temperature is compensated either by controlling the temperature of the electrode, or by monitoring the temperature and correcting the meter readout electronically.

The most common prior art approach to temperature monitoring is to place a thermistor (or a like device) in the cable connecting the electrode to the meter. In this configuration, the thermistor is placed in proximity to the liquid electrolyte or to the cathode, thereby being somewhat insulated from the room air temperature, and giving a representation of working temperature at the cathode-electrode-membrane location. It is evident, however, that such location for the thermistor cannot be totally accurate because of its spatial disparity from the reaction site. On the other hand, electrical separation must be maintained between the electrochemical cell and the temperature sensor, lest the latter have an effect on the operation of the former.

THE PRESENT INVENTION

It is a primary object of the present invention to provide improved temperature sensing mechanisms for electrochemical cells such as polarographic sensors.

It is a further object to provide temperature compensation mechanisms for disposable ones of such cells, wherein expensive temperature sensing components are thermally coupled to but spatially isolated from the fluids being sensed.

It is a still further object to provide temperature sensors for disposable electrodes which substantially reduce the temperature control/correction response time.

These and other objects are substantially achieved in accordance with the principles of the present invention, wherein an electrical sensor includes a housing defining a passageway for fluids to be monitored, suitable electrodes, electrolytes, and membrane for the actual electrochemical cell, and a temperature sensing means distinct from but proximate the electrode, penetrating the housing and being in direct thermal contact with the fluid (blood, gas, etc.) in the passageway. If gases such as air or anesthetic mixtures are being monitored, the temperature sensing means extends directly into the passageway and in the gas flow, whereas if blood or the like liquids are being sensed, the temperature sensing means is advantageously located along the passageway wall, but still in thermal contact with the fluid. For purposes of disposable electrodes, the temperature sensing means employs a thermally conductive (e.g. metallic) portion which is integral with the housing and which contacts the fluid, and a removable thermistor which makes contact with the metal and thereby is in thermal contact, but spatial isolation, from the fluid.

DESCRIPTION OF THE DRAWINGS

FIG. 1 shows an isometric top view of an illustrative embodiment of the present invention.

FIG. 2 shows a side cutaway view of the embodiment of FIG. 1, illustrating a preferred temperature sensing assembly for blood gas sensors in accordance with the principles of the present invention.

FIG. 3 shows an enlarged view of the temperature sensing aspect of the embodiment of FIG. 2.

FIG. 4 shows an alternative temperature sensing scheme in accordance with the principles of the present invention, adapted for sensors operable upon gases.

BEST MODE OF CARRYING OUT THE INVENTION

Referring first to FIGS. 1 through 3, there is shown a preferred embodiment of the principles of the present invention, specifically adapted to electrochemical sensors for sensing partial pressures of gases such as oxygen in blood. In particular, the sensor configuration as set forth in FIGS. 1–3, particularly FIG. 2, involves a polarographic cell of the type set forth in the aforementioned U.S. Pat. No. 3,826,730 to Watanabe et al. Such cells are particularly useful for extracorporeal monitoring of blood gases during surgery. A housing 101 defines therein a passageway 102 for the flow of fluids. In the drawing, fluid flow is shown to pass first by a temperature sensor and thence to an electrochemical cell, but it is understood that for specific other applications, the opposite may be true. Likewise, the embodiment of FIGS. 1–3 discloses a temperature sensing assembly which is substantially adjacent the electrochemical cell. It is to be understood that in accordance with the needs of those of ordinary skill in the art, the temperature sensing assembly may be otherwise located on the housing 101 relative to the electrochemical cell, for example diametrically opposite the passageway 102. As shown, the housing 101 defines two openings 103 and 118, the former of which carries a polarographic cell, and the latter of which carries a temperature sensing assembly. Both the cell and the temperature sensing assembly involve portions which are disposable along with the housing 101, and portions which are removable from the unit for reuse with subsequent units.

Rigidly permanently connected to the housing 101 and penetrating opening 103 is the disposable portion 108 of the electrode, including an anode assembly 106, a cathode assembly 107, a selectively permeable membrane 105, and a closure 113. The upper portion of the cartridge 108 defines screw threading 109, which is adapted matably to engage with a retaining nut or collar 111 which is associated with a reusable cable-electrode assembly 112. This detachable, reusable cable assembly includes an anode connector 114 and a cathode connector 115, the latter being immersed in an electrolyte 116 but making electrical contact with the cathode assembly 107.

Hence, in a manner conventional in the art, the cable assembly 112 is mounted with terminals 114 and 115 penetrating cartridge top closure 113, and the retaining nut or collar 111 is screw tightened down onto the disposable portion 108 as shown by means of the threaded engagement thereof. Radially raised portions 128 on the retaining nut 111 facilitate this tightening or removal action, whereby the collar or nut 111, the cable assembly 112, and the electrode connectors 114 and 115 may be reused, as desired, with subsequent sensors.

The present invention involves temperature sensors useful in conjunction with the cells as described herein, whereby temperature compensation may be accomplished, as is known in the art, either by local temperature control, or, more preferably, by electronic computational compensation at the electronics-metering aspects of the system.

As may be seen most clearly from FIG. 3, the opening 118 in housing 101 is occupied by a heat transfer disk 119, advantageously stainless steel. The disk is preferably ultrasonically swaged into the housing 101, optionally further utilizing a silicone rubber gasket 127, but it is to be understood that the disk 119 may be mounted onto the housing 101 in a variety of ways which are known in the art and which prevent leakage out of the passageway 102 of the fluid being monitored.

On the side of the disk 119 opposite the passageway 102 is a thermistor assembly which is in thermal contact with the disk 119. It is to be understood that the term "thermistor" or "thermistor means" is used herein to embody the active temperature sensing components, but that numerous functional alternatives could as well be used (e.g. thermocouple, etc.).

As shown, the thermistor assembly includes a chassis 117 having a cylindrical portion 129 to house the actual thermistor. Within the cylindrical housing 129 is a thermally conductive potting compound 120 enclosing the thermistor 121, sealed at the top with a thermally non-conductive potting compound 123. The thermistor 121 is coupled, by means of an electrical conductor 122, to external apparatus for translating the signal generated at the thermistor 121 into useful control signals. The electrical conductor 122 is contained within by a suitable electrically insulating jacket material 131, from a point within the non-conductive potting compound 123, out to the external metering apparatus (not shown). A deformable washer or gasket 124 seals the interface between disk 119 and conductive potting compound 120 from the exterior, and in view of the essentially thermally non-conductive characteristics of housing 101, washer 124, chassis 117, and potting compound 123, the disk 119—compound 120—thermistor 121 combination operates to sense the temperature of the fluid in the passageway 102. That is, the thermistor 121 is in "thermal contact" with the fluid in passageway 102 (although spatially isolated therefrom).

As may be seen most clearly in FIGS. 1–3, the chassis 117 includes an annular portion which envelops the electrochemical sensor cartridge 108, and which is maintained tightly in position by the screw closure of the retaining nut 111 about the cartridge 108. It is this screw closure bearing down on the annular portion of chassis 117 which sealingly deforms the raised annulus 130 of housing 101 into the deformable washer 124, and which thereby maintains the entire thermistor assembly in position with the thermally conductive potting compound 120 being in thermally conductive relationship with the disk 119. Upon loosening of the retaining nut 111 and removal of the anode cable assembly 112, the entire chassis 117 of the temperature sensing assembly may be removed for purposes of reuse, taking with it the potted portions 120 and 123, and the thermistor 121 which is encased therein.

It will be apparent that the embodiment of FIGS. 1–3 is configured for operation with any fluid (liquid or gas), with minimal impedence to flow of such fluid within the passageway 102. For use with blood, which has a tendency to clot at discontinuities, it may further be desirable, but not essential, to blunt the edges 125 of opening 118, to the rounded configuration 126 shown in phantom in FIG. 3. Likewise, the disk 119 may be flush with the walls of passageway 102.

In the event that gases are being evaluated in the passageway 102, the alternate configuration of FIG. 4 may be employed, wherein a thermally conductive member 219 fulfills the function of disk 119 in FIGS. 1–3. That is, the cuplike conductive member 219 is thermally conductive, protrudes into the passageway 102, and includes an inner surface for receipt of the thermistor assembly (which includes the chassis 217, cylindrical portion 229, respective thermally conductive and non-conductive compounds 220 and 223, thermistor 221 and electrical conductor 222). An optional silicone rubber gasket 227 is provided, and a deformable washer or gasket 224 sealingly engages chassis 217 to raised annular portion 230 of the housing 201. Alternatively, the conductive member may involve a solid thermally conductive protuberance into passageway 102, with portion 220 in contact therewith at a convenient location outside the passageway.

In preferred embodiments, the following materials are utilized, but it is to be understood that many alternatives are commercially available and known in the art. The temperature sensing device 121 and 221 is a thermistor of the type available from Fenwal Electronics under the trade designation UUT51J35, or alternatively a thermocouple commercially available from Omega Engineering under the trade designation NN-T-24. The disk 119 and cup 219 are preferably embodied as stainless steel, but it is to be understood that where compatibility with the fluid being analyzed so permits, other materials with similar thermal properties may be employed. For example, where blood compatibility is not required, aluminum may be substituted for stainless steel for the disk 119 or the cup 219. A preferred thermally conductive potting compound 120 and 220 is that available from Emerson and Cuming, Inc. under the trade designation Eccobond 285, and a similarly preferred non-conductive potting compound 123 and 223 is that available from Emerson and Cuming, Inc. under the trade designation Eccobond SF-40. Numerous alternative compositions are commercially available and well known to those of ordinary skill in the art. The chassis 117 or 217 is preferably composed of a suitably rigid, thermally non-conductive material such as polypropylene, polyethylene, nylon, or many others.

It will be understood that the foregoing discloses preferred and illustrative embodiments of the principles of the present invention, but the numerous alternative embodiments will occur to those of ordinary skill in the art without departure from the spirit or the scope of the present invention.

I claim:

1. An electrochemical sensor comprising:
   a housing defining a passageway for fluids to be monitored;
   at least one electrode;
   a membrane in said housing separating said electrode from fluid in said passageway;
   and characterized by temperature sensing means, proximate said membrane, penetrating said housing and being in direct thermal contact with fluid in said passageway,
   wherein said temperature sensing means comprises a removable collar carrying thermistor means, said collar being sealably matably received by said housing means to hold said thermistor means in direct thermal contact with said fluid, whereby said sensor is disposable but said temperature sensing means is reusable,
   wherein said electrode includes a disposable portion carried by said housing and a reusable portion contactable with said disposable portion, wherein said housing includes an outwardly raised boss surrounding said disposable electrode portion, wherein said reusable electrode portion includes a collar for matable sealing engagement with said boss, and wherein said thermistor means collar includes a protuberance removably held between said boss and said electrode collar.

2. A sensor as described in claim 1 wherein said boss and said electrode collar are generally cylindrical, and wherein said protuberance includes an annular portion matable about said boss.

3. An electrochemical sensor comprising:
   a housing defining a passageway for fluids to be monitored;
   at least one electrode;
   a membrane in said housing separating said electrode from fluid in said passageway;
   and characterized by temperature sensing means, proximate said membrane, penetrating said housing and being in direct thermal contact with fluid in said passageway,
   wherein said fluid is gas,
   wherein said temperature sensing means includes a thermally conductive portion extending directly into said passageway in the gas flow, and thermistor means in thermal contact with said thermally conductive portion, and
   wherein said thermistor means comprises a removable collar carrying a thermistor, said collar being sealably matably received by said housing means to hold said thermistor in contact with said thermally conductive portion, whereby said sensor, including said thermally conductive portion, is disposable but said thermistor means is reusable.

4. An electrochemical sensor comprising:
   a housing defining a passageway for fluids to be monitored;
   at least one electrode;
   a membrane in said housing separating said electrode from fluid in said passageway;
   and characterized by temperature sensing means, proximate said membrane, penetrating said housing and being in direct thermal contact with fluid in said passageway,
   wherein said fluid is liquid,
   wherein said temperature sensing means comprises a thermally conductive portion affixed to and generally conforming with the walls of said housing defining said passageway, and thermistor means in thermal contact with said thermally conductive portion, and
   wherein said thermistor means comprises a removable collar carrying a thermistor, said collar being sealably matably received by said housing means to hold said thermistor in contact with said thermally conductive portion, whereby said sensor, including said thermally conductive portion, is disposable but said thermistor means is reusable.

5. An electrochemical sensor for monitoring partial pressure of select gases in a moving fluid comprising:
   a housing defining a passageway through which fluids to be monitored are passed;
   at least one electrode;
   a membrane in said housing along the fluid flow path and separating said electrode from fluid in said passageway;
   and temperature sensing means, proximate said membrane, penetrating said housing along the fluid flow path and being in direct thermal contact with fluid in said passageway, wherein said fluid is liquid and wherein said temperature sensing means comprises a thermally conductive portion affixed to and generally conforming with the walls of said housing defining said passageway, and thermistor means in thermal contact with said thermally conductive portion, wherein said fluid is blood, and wherein said passageway and said thermally conductive portion are mutually configured with minimum discontinuities thereby to prevent clotting in said passageway, wherein said thermally conductive portion includes a thermally conductive plate member imbedded in the walls of said housing slightly recessed from said passageway, wherein the edges of said passageway communicating with said plate member are rounded to prevent clotting of blood at the portion of the housing surrounding said plate member.

* * * * *